(12) United States Patent
Parker

(10) Patent No.: US 12,064,620 B2
(45) Date of Patent: *Aug. 20, 2024

(54) NEURAL STIMULATION DOSING

(71) Applicant: Saluda Medical Pty Ltd, Level (AU)

(72) Inventor: John Louis Parker, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/317,715

(22) Filed: May 15, 2023

(65) Prior Publication Data

US 2023/0364417 A1 Nov. 16, 2023

Related U.S. Application Data

(63) Continuation of application No. 17/234,678, filed on Apr. 19, 2021, now abandoned, which is a continuation of application No. 16/823,296, filed on Mar. 18, 2020, now Pat. No. 11,167,129, which is a continuation of application No. 15/327,981, filed as application No. PCT/AU2015/050422 on Jul. 27, 2015, now Pat. No. 10,632,307.

(30) Foreign Application Priority Data

Jul. 25, 2014 (AU) .................................. 2014902897
Mar. 13, 2015 (AU) .................................. 2015900912

(51) Int. Cl.
*A61N 1/05* (2006.01)
*A61N 1/06* (2006.01)
*A61N 1/36* (2006.01)
*A61N 1/372* (2006.01)

(52) U.S. Cl.
CPC ............. *A61N 1/0551* (2013.01); *A61N 1/05* (2013.01); *A61N 1/06* (2013.01); *A61N 1/3605* (2013.01); *A61N 1/36071* (2013.01); *A61N 1/36146* (2013.01); *A61N 1/36171* (2013.01); *A61N 1/36175* (2013.01); *A61N 1/36178* (2013.01); *A61N 1/36185* (2013.01); *A61N 1/37247* (2013.01); *A61N 1/36021* (2013.01)

(58) Field of Classification Search
CPC ................................ A61N 1/0551; A61N 1/05
USPC .......................................................... 607/46
See application file for complete search history.

(56) References Cited

U.S. PATENT DOCUMENTS 7,634,315 B2 12/2009 Cholette
8,688,221 B2 4/2014 Miesel et al.
(Continued)

FOREIGN PATENT DOCUMENTS

WO 2004002572 A1 1/2004
WO 2004034879 A3 7/2004
(Continued)

*Primary Examiner* — Nadia A Mahmood
(74) *Attorney, Agent, or Firm* — Barnes & Thornburg LLP

(57) ABSTRACT

Applying therapeutic neural stimuli involves monitoring for at least one of sensory input and movement of a user. In response to detection of sensory input or user movement, an increased stimulus dosage is delivered within a period of time corresponding to a duration of time for which the detected sensory input or user movement gives rise to masking, the increased stimulus dosage being configured to give rise to increased neural recruitment.

20 Claims, 11 Drawing Sheets

(56) References Cited

U.S. PATENT DOCUMENTS

| | | |
|---|---|---|
| 10,201,705 B2 | 2/2019 | Bharmi et al. |
| 11,247,057 B1 | 2/2022 | Gliner |
| 11,684,774 B2 | 6/2023 | Crosby et al. |
| 2020/0353263 A1 | 11/2020 | Parker et al. |
| 2022/0241592 A1 | 8/2022 | Sachs et al. |
| 2022/0347480 A1 | 11/2022 | Sachs et al. |
| 2023/0067424 A1 | 3/2023 | Crosby et al. |

FOREIGN PATENT DOCUMENTS

| | | | | |
|---|---|---|---|---|
| WO | 2005089646 A1 | 9/2005 | | |
| WO | 2007087560 A3 | 9/2008 | | |
| WO | 2009042379 A1 | 4/2009 | | |
| WO | 2009137119 A1 | 11/2009 | | |
| WO | 2010005777 A1 | 1/2010 | | |
| WO | 2011112773 A3 | 12/2011 | | |
| WO | 2012155183 A1 | 11/2012 | | |
| WO | 2012155188 A1 | 11/2012 | | |
| WO | 2012155189 A1 | 11/2012 | | |
| WO | WO-2012155188 A1 * | 11/2012 | ......... | A61B 5/04001 |
| WO | 2013028680 A3 | 6/2013 | | |
| WO | 2015070281 A1 | 5/2015 | | |
| WO | 2015143509 A1 | 10/2015 | | |
| WO | 2015066617 A9 | 11/2015 | | |
| WO | 2016077882 A1 | 5/2016 | | |

* cited by examiner

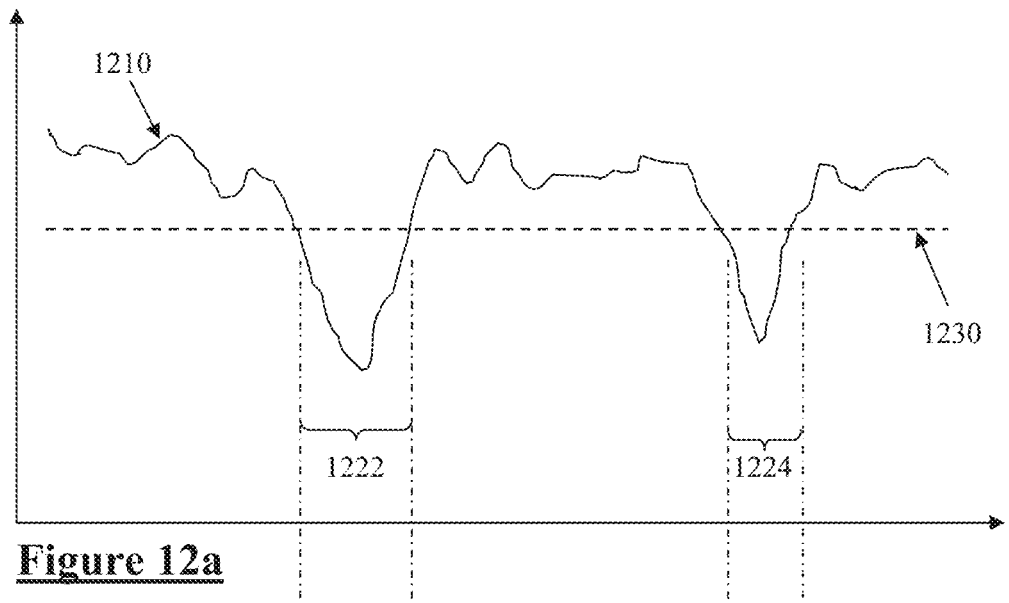
Figure 12a
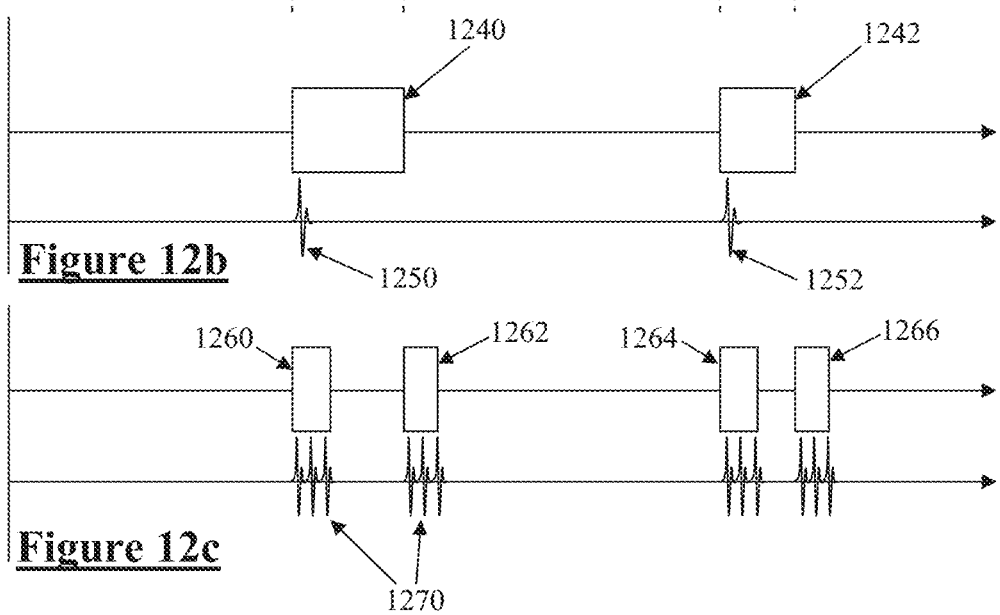
Figure 12b
Figure 12c

NEURAL STIMULATION DOSING

CROSS-REFERENCE TO RELATED APPLICATIONS

The current application is a continuation of U.S. patent application Ser. No. 17/234,678 entitled "Neural Stimulation Dosing" to John Louis Parker, filed Apr. 19, 2021, which application is a continuation of U.S. patent application Ser. No. 16/823,296, entitled "Neural Stimulation Dosing" to John Louis Parker, filed Mar. 18, 2020, which application is a continuation of U.S. patent application Ser. No. 15/327,981, entitled "Neural Stimulation Dosing" to John Louis Parker, filed Jan. 20, 2017 and issued on Apr. 28, 2020 as U.S. Pat. No. 10,632,307, which application is a 35 U.S.C. § 371 National Stage Patent Application of PCT Patent Application Serial No. PCT/AU2015/050422 entitled "Neural Stimulation Dosing" to John Louis Parker, filed Jul. 27, 2015, which application claims priority to Australian Patent Application Serial No. 2014902897, filed Jul. 25, 2014 and Australian Patent Application Serial No. 2015900912, filed Mar. 13, 2015, the disclosures of which are hereby incorporated by reference in their entireties for all purposes.

TECHNICAL FIELD

The present invention relates to the application of therapeutic neural stimuli, and in particular relates to applying a desired dose of stimuli by using one or more electrodes implanted proximal to the neural pathway in a variable manner to minimise adverse effects.

BACKGROUND OF THE INVENTION

There are a range of situations in which it is desirable to apply neural stimuli in order to give rise to a compound action potential (CAP). For example, neuromodulation is used to treat a variety of disorders including chronic neuropathic pain, Parkinson's disease, and migraine. A neuromodulation system applies an electrical pulse to tissue in order to generate a therapeutic effect.

When used to relieve neuropathic pain originating in the trunk and limbs, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and the generation of propagating action potentials. The fibres being stimulated in this way inhibit the transmission of pain from that segment in the spinal cord to the brain. To sustain the pain relief effects, stimuli are applied substantially continuously, for example at a frequency in the range of 30 Hz-100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin.

For effective and comfortable operation, it is necessary to maintain stimuli amplitude or delivered charge above a recruitment threshold. Stimuli below the recruitment threshold will fail to recruit any action potentials. It is also necessary to apply stimuli which are below a comfort threshold, above which uncomfortable or painful percepts arise due to increasing recruitment of Aβ fibres which when recruitment is too large produce uncomfortable sensations and at high stimulation levels may even recruit sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if afferent or efferent motor fibres are recruited. The task of maintaining appropriate neural recruitment is made more difficult by electrode migration and/or postural changes of the implant recipient, either of which can significantly alter the neural recruitment arising from a given stimulus, depending on whether the stimulus is applied before or after the change in electrode position or user posture. There is room in the epidural space for the electrode array to move, and such array movement alters the electrode-to-fibre distance and thus the recruitment efficacy of a given stimulus. Moreover the spinal cord itself can move within the cerebrospinal fluid (CSF) with respect to the dura. During postural changes the amount of CSF and the distance between the spinal cord and the electrode can change significantly. This effect is so large that postural changes alone can cause a previously comfortable and effective stimulus regime to become either ineffectual or painful.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of applying therapeutic neural stimuli, the method comprising:
  monitoring for at least one of sensory input and movement of a user; and
  in response to detection of at least one of sensory input and a user movement, delivering an increased stimulus dosage within a period of time corresponding to a duration of time for which the detected sensory input or user movement gives rise to masking, the increased stimulus dosage being configured to give rise to increased neural recruitment.

According to a second aspect the present invention provides a device for applying therapeutic neural stimuli, the device comprising:
  at least one electrode configured to be positioned alongside a neural pathway of a user; and
  a control unit configured to monitor for at least one of sensory input and movement of the user, and configured to deliver, in response to detection of at least one of sensory input and a user movement, an increased stimulus dosage via the at least one electrode within a period of time corresponding to a duration of time for which the detected sensory input or user movement gives rise to masking, the increased stimulus dosage being configured to give rise to increased neural recruitment.

The first and second aspects of the present invention recognise that during movement or sensory input the psychophysics of perception can result in the individual perceiving a reduced sensation from a given stimulus as compared to when the same stimulus is applied while the individual is not moving nor receiving sensory input. However, the benefits of delivering a large dosage of stimuli remain for a period of time after conclusion of the stimuli. The first and second aspects of the present invention thus recognise that periods of time during which the user is moving or receiving sensory input present an opportunity to deliver an increased dosage of stimulation.

In some embodiments of the first and second aspects of the invention, the increased stimulus dosage may be effected by increasing one or more of the stimulus amplitude, the stimulus pulse width and/or the stimulus frequency. The increased stimulus dosage may for example comprise a burst of high frequency stimuli, for example stimuli at 10 kHz, 40 µs pulse width and 2 mA amplitude. At times when neither sensory input nor movement is detected stimuli may be delivered at a reduced dosage, for example at 20 or 30 Hz, or even not at all.

In some embodiments, a cumulative stimulus dosage delivered to the user may be monitored, and may be used as a basis to define a required stimulus regime during periods of sensory input or movement, and/or during periods of no sensory input and no movement, in order to seek to deliver a desired total stimulus dosage over the course of a dosage period such as an hour or a day.

In some embodiments, sensory input or movement of the user is detected by measuring neural activity upon the neural pathway. The measured neural activity may comprise evoked neural responses resulting from electrical stimuli applied to the neural pathway, and for example sensory input or movement may be detected when a change is detected in the neural response evoked from a given stimulus. The measured neural activity may additionally or alternatively comprise non-evoked neural activity, being the neural activity present on the neural pathway for reasons other than the application of electrical stimuli by the device. Such embodiments recognise that non-evoked neural activity rises significantly during periods of sensory input or user movement, so that an observed increase or alteration in non-evoked neural activity can be taken to indicate sensory input or user movement.

In other embodiments, movement of the user may be detected by an accelerometer or other movement detector.

The period of time within which the increased stimulus dosage is delivered may be predefined as an approximation of the duration of a typical human movement, and for example may be predefined to be of the order of one second in duration. Additionally or alternatively, the period of time for which the increased stimulus dosage is delivered may be adaptively determined by performing the further step of detecting a cessation of sensory input or movement of the user, and in turn ceasing the delivery of the increased stimulus dosage.

Additionally or alternatively, the period of time for which the increased stimulus dosage is delivered may be predefined or adaptively determined to take a value corresponding to the typical duration of non-evoked neural activity. For example, in some embodiments the period of time for which the increased stimulus dosage is delivered may be in the range 10-100 ms, or more preferably 20-40 ms, more preferably around 30 ms. In such embodiments the increase in stimulus dosage may involve imposing an increased frequency of stimulation, for example by increasing a frequency of stimulation from 60 Hz to 1 kHz in order to deliver around 30 stimuli during a 30 ms window of non-evoked neural activity rather than delivering only about 2 stimuli as would occur at 60 Hz.

Additionally or alternatively, the period of time for which the increased stimulus dosage is delivered and/or a stimulus strength of the increased stimulus dosage may be adaptively determined by performing the further step of measuring a strength of the movement or sensory input, and determining the period of time and/or the stimulus strength from the movement strength, for example the period of time and/or the stimulus strength may be made to be proportional to the movement strength. The movement or sensory strength may for example comprise a magnitude or power of the detected movement or sensory input, or other strength measure of the detected movement or sensory input. In such embodiments the stimulus strength may be controlled to remain below a threshold for sensation by a certain amount or fraction, over time as the threshold for sensation varies with movement or sensory input, to thereby avoid or minimise the stimuli causing a paraesthesia sensation while maintaining a therapeutic dose of the stimuli.

The increased stimulus dosage may be delivered throughout the period of time or at select moments within the period of time such as only at the commencement and/or cessation of the sensory input or movement or the period of time.

According to a third aspect the present invention provides a method for effecting a neural blockade, the method comprising:

delivering a sequence of electrical stimuli to neural tissue, each stimulus configured at a level whereby at least at a given relative position of a stimulus electrode to the neural tissue a first stimulus of the sequence generates an action potential and whereby each subsequent stimulus alters a membrane potential of the neural tissue without causing depolarisation of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

According to a fourth aspect the present invention provides a device for effecting a neural blockade, the device comprising:

at least one electrode configured to be positioned alongside a neural pathway of a user; and a control unit configured to deliver a sequence of electrical stimuli to neural tissue, each stimulus configured at a level whereby at least at a given relative position of the electrode to the neural tissue a first stimulus of the sequence generates an action potential and whereby each subsequent stimulus alters a membrane potential of the neural tissue without causing depolarisation of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

Embodiments of the third and fourth aspects of the invention thus apply a sequence of stimuli which at first produce an action potential and which then create a blockade, the blockade arising during the period in which the sequence of stimuli maintains the membrane potential in an altered range in which conduction of action potentials is hindered or prevented. In some embodiments a blockade may be effected by applying a sequence of supra-threshold stimuli, the first of which will evoke an action potential. Additional or alternative embodiments may effect a blockade by applying a sequence of stimuli which are sub-threshold in a first posture, but which become supra-threshold at times when the user moves to a second posture. In such embodiments, the first stimulus delivered after the stimulus threshold falls below the stimulus amplitude will evoke an action potential. Blockading is beneficial because the stimuli delivered during the blockade evoke few or no action potentials at the stimulus site and will thus give rise to a significantly reduced effect of, or even a complete absence of, paresthesia.

In some embodiments of the third and fourth aspects of the invention, the sequence of stimuli may be delivered at a frequency, or an average frequency, which is greater than 500 Hz, more preferably greater than 1 kHz, and for example may be in the range of 5-15 kHz. In some embodiments the frequency may be defined by determining an average refractory period of the subject, such as by using the techniques of International Patent Application Publication No. WO2012155189, the contents of which are incorporated herein by reference. The frequency of the delivered stimuli may then be set so that the inter-stimulus time is less than the determined refractory period, or is a suitable fraction or multiple thereof.

In some embodiments of the third and fourth aspects of the invention, the nominal sub-threshold level may be pre-determined for example by a clinician at a time of fitting of an implanted stimulator for the user. The nominal sub-threshold level is in some embodiments set at a level which is a large fraction of a stimulus threshold in a given posture, for example being 50%, 75% or 90% as large as the stimulus threshold in that posture. The nominal sub-threshold level may be adaptively determined, for example by repeatedly determining a recruitment threshold of the neural tissue from time to time, such as by measuring neural responses evoked by stimuli, and re-setting the nominal sub-threshold level by reference to a most recent determined threshold level. The recruitment threshold of the neural tissue is in some embodiments determined at time intervals which are substantially greater than the duration of a typical human movement so as to allow the neural blockade to be established during a movement.

Some embodiments of the invention may implement blockading in accordance with the third aspect of the invention only at times of detected sensory input or movement, in accordance with the first aspect of the invention. In such embodiments, the detection of sensory input or movement may be effected by delivering the blockade stimuli continuously at the nominal sub-threshold level, whereby the blockade stimuli come into effect only during sensory input or movements which cause the momentary recruitment threshold to fall below the nominal sub-threshold level. Alternatively, in such embodiments the blockading may be commenced in response to detection of sensory input or movement so that the action potential generated by the first stimulus of the sequence is masked by the sensory input or movement.

According to a fifth aspect the present invention provides a computer program product comprising computer program code means to make a computer execute a procedure for applying therapeutic neural stimuli, the computer program product comprising:
  computer program code means for monitoring for at least one of sensory input and movement of a user; and
  computer program code means for, in response to detection of at least one of sensory input and a user movement, delivering an increased stimulus dosage within a period of time corresponding to a duration of time for which the detected sensory input or user movement gives rise to masking, the increased stimulus dosage being configured to give rise to increased neural recruitment.

According to a sixth aspect the present invention provides a computer program product comprising computer program code means to make a computer execute a procedure for effecting a neural blockade, the computer program product comprising:
  computer program code means for delivering a sequence of electrical stimuli to neural tissue, each stimulus configured at a level whereby at least at a given relative position of a stimulus electrode to the neural tissue a first stimulus of the sequence generates an action potential and whereby each subsequent stimulus alters a membrane potential of the neural tissue without causing depolarisation of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

In some embodiments of the fifth and sixth aspects of the invention, the computer program product comprises a non-transitory computer readable medium comprising instructions for execution by one or more processors.

BRIEF DESCRIPTION OF THE DRAWINGS

An example of the invention will now be described with reference to the accompanying drawings, in which.

FIGS. 12a, 12b, and 12c illustrate stimulus regimes applied in accordance with some embodiments of the present invention;

DESCRIPTION OF THE PREFERRED EMBODIMENTS

Figure 1:
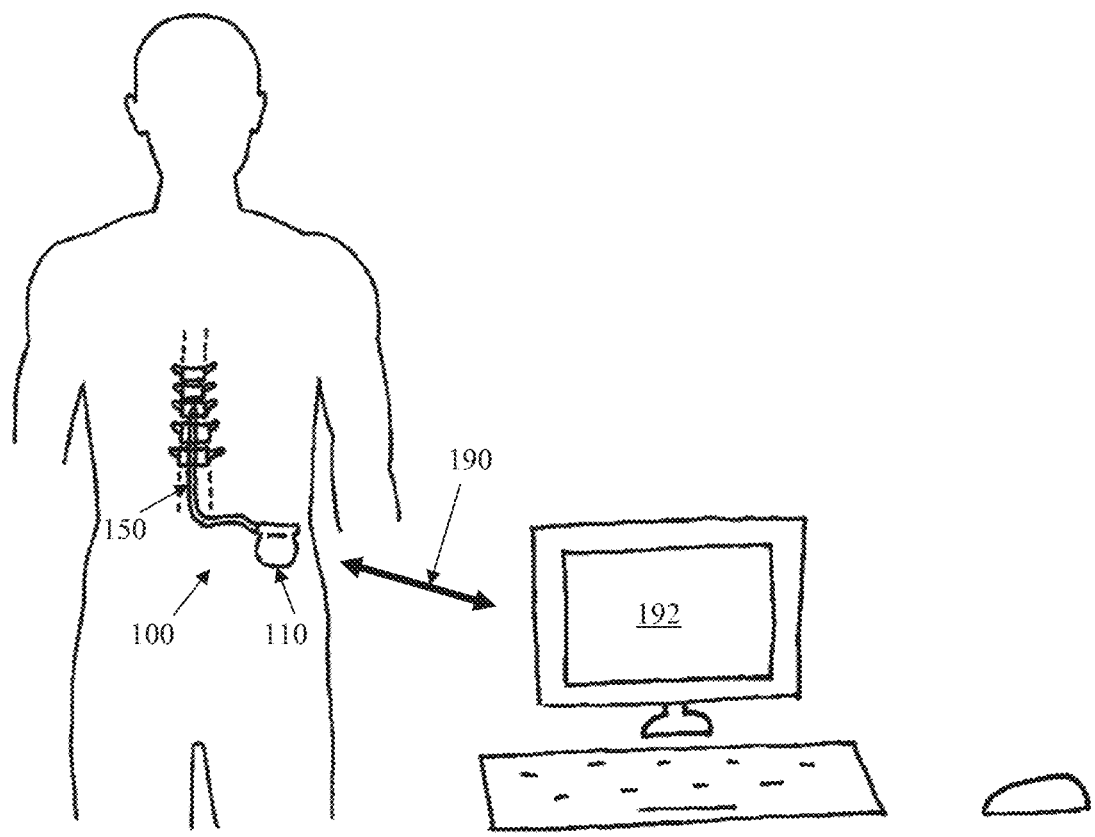
FIG. 1 schematically illustrates an implanted spinal cord stimulator.

FIG. 1 schematically illustrates an implanted spinal cord stimulator 100. Stimulator 100 comprises an electronics module 110 implanted at a suitable location in the patient's lower abdominal area or posterior superior gluteal region, and an electrode assembly 150 implanted within the epidural space and connected to the module 110 by a suitable lead. Numerous aspects of operation of implanted neural device 100 are reconfigurable by an external control device 192. Moreover, implanted neural device 100 serves a data gathering role, with gathered data being communicated to external device 192.

Figure 2:
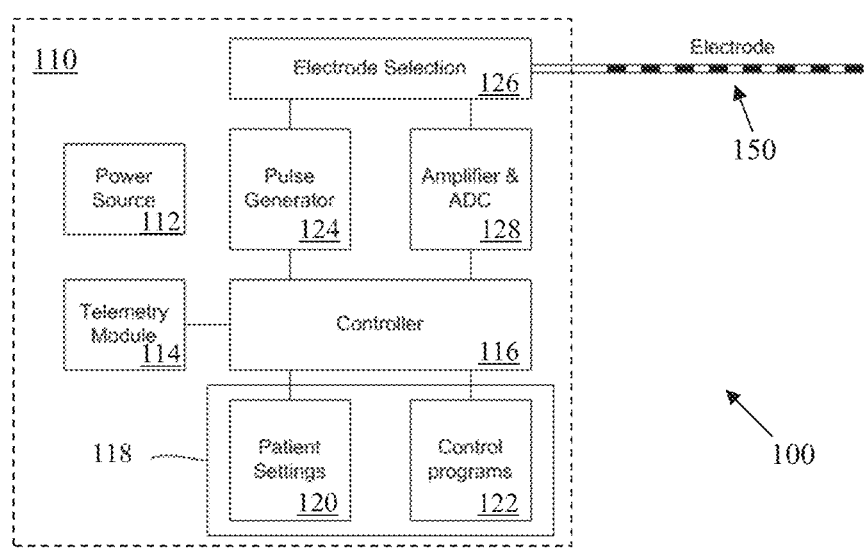
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). Measurement circuitry 128 is configured to capture measurements of neural responses sensed at sense electrode(s) of the electrode array as selected by electrode selection module 126.

Figure 3:
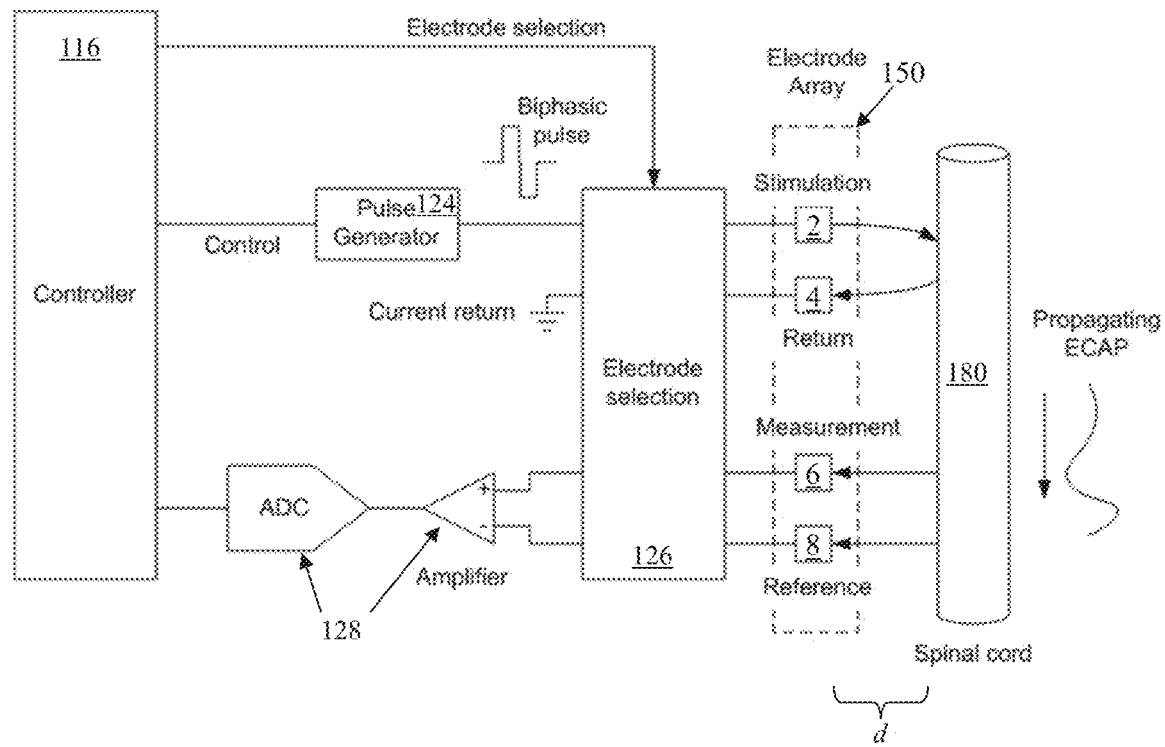
FIG. 3 is a schematic illustrating interaction of the implanted stimulator with a nerve.

FIG. 3 is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. Electrode selection module 126 selects a stimulation electrode 2 of electrode array 150 to deliver an electrical current pulse to surrounding tissue including nerve 180, and also selects a return electrode 4 of the array 150 for stimulus current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of a spinal cord stimulator for chronic pain might be to create paraesthesia at a desired location. To this end the stimulus electrodes are used to deliver stimuli at 30 Hz. To fit the device, a clinician applies stimuli which produce a sensation that is experienced by the user as a paraesthesia. When the paraesthesia is in a location and of a size which is congruent with the area of the user's body affected by pain, the clinician nominates that configuration for ongoing use.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

However the present invention recognises that it is unclear whether or not the experience of parestheisa is necessary for pain reduction on an ongoing basis. Although paraesthesia is generally not an unpleasant sensation there may nevertheless be benefits in a stimulus regime which provides pain relief without the generation of sensation.

Figure 4:
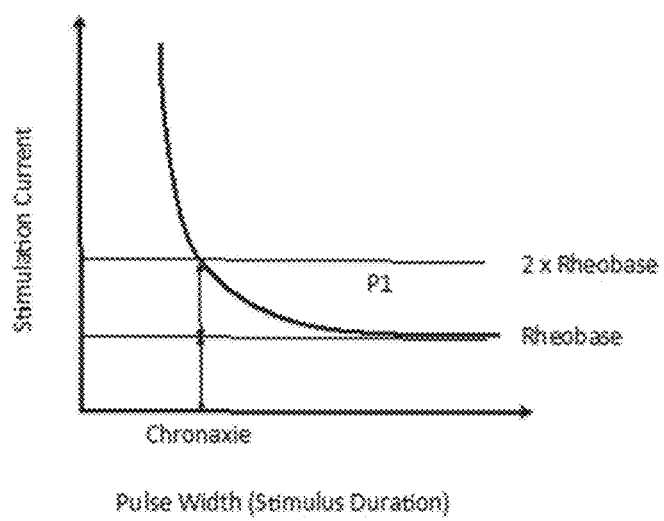
FIG. 4 illustrates the strength duration curve followed by the threshold for action potential generation in an axon.

The threshold for action potential generation in an axon follows the strength duration curve as shown in FIG. 4. As the pulse width of the stimulus is increased the current needed for an axon to reach threshold decreases. The Rheobase current is an asymptotic value, being the largest current that is incapable of producing an action potential even at very long pulse widths. The Chronaxie is then defined as the minimum pulse width required to evoke an action potential at a current that is twice the Rheobase current.

Figure 5:
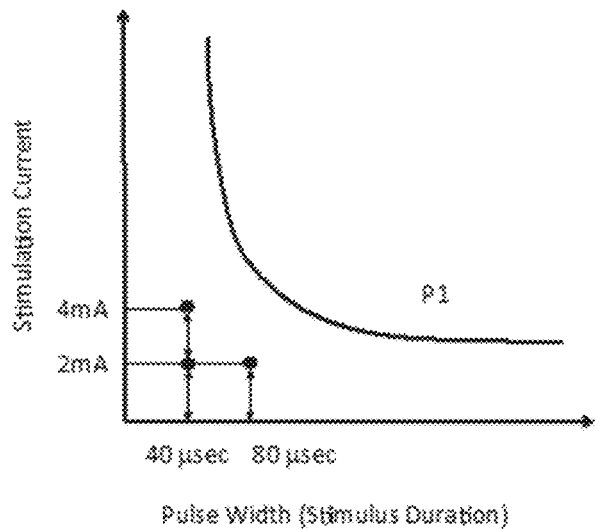
FIG. 5 illustrates the effect on the strength duration curve of delivering a high frequency pulse train.

FIG. 5 illustrates the effect on the strength duration curve of delivering a high frequency pulse train. As shown, a high frequency pulse train can effectively act as a single pulse with a longer pulse width with respect to activating a nerve. That is, closely spaced stimuli can effectively add up and recruit additional populations of fibres when compared with widely spaced stimuli with the same pulse width. Stimuli can either depolarize axon membranes to threshold and generate action potentials, or they can depolarize the axon membrane potential just below threshold and not produce an action potential. When an axon produces an action potential in response to a stimulus it is unable to produce a second potential for a period of time called the refractory period. On the other hand, those axons that did not reach threshold in response to the first stimulus may reach threshold on subsequent stimuli as their membrane potential is raised closer and closer to threshold with every stimulus, provided that the next stimuli occurs prior to recovery of the membrane potential from the previous stimuli. This effect equilibrates over a small number of high frequency stimuli, and may account for an effective doubling of the number of fibres recruited, when compared with a single stimulus of the same pulse width at low frequency.

Figure 6:
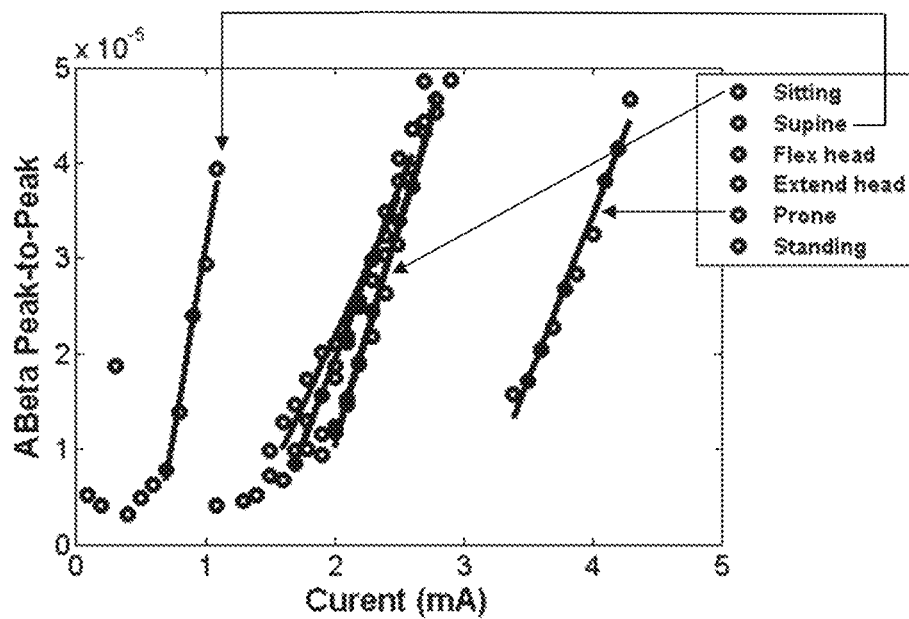
FIG. 6 shows the amplitude growth curves for an individual at a number of different postures.

Activation of Aβ fibres in the dorsal column can vary considerably in response to changes in posture. This postural affect is primarily due to the movement of the stimulus electrodes with respect to the fibres. Changes in posture can be measured by recording the evoked compound action potential (ECAP). Momentary changes in posture, for instance a sneeze or a cough, can produce a factor of 10 increase in the amplitude of an evoked CAP, or more. FIG. 6 shows the amplitude growth curves for an individual at a number of different postures. It demonstrates a significant change in recruitment threshold as the patient moves from one posture to another, with the recruitment threshold being almost as low as 0.5 mA when the user is lying supine and being about 3 mA when the user is lying prone.

Figure 7:
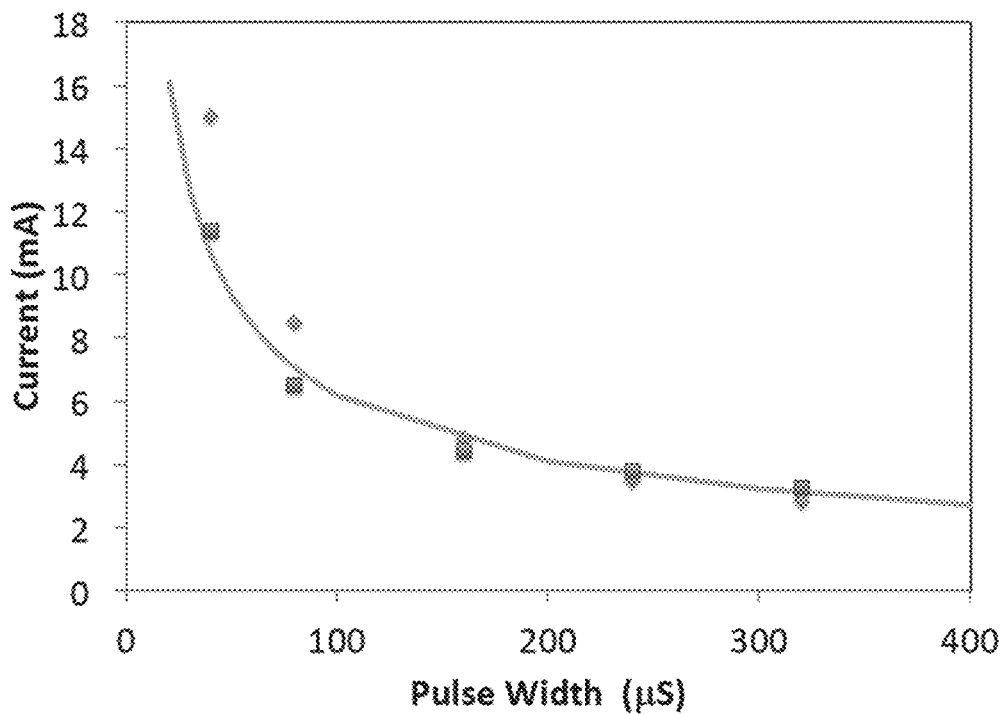
FIG. 7 shows the strength duration curve corresponding to the activation of the dorsal columns.

FIG. 7 shows the strength duration curve corresponding to the activation of the dorsal columns for a single posture. The current corresponding to the threshold for an ECAP versus the pulse width. For example a pulse width of 35 μs corresponds to a threshold current of 11.5 mA. Noting the recruitment curves of FIG. 6, when the sitting patient moves to a supine position the threshold in FIG. 7 could be expected to drop to a third of the value, which for a pulse width of 35 μs indicates that the threshold will be 11.5/3=3.83 mA. To maintain threshold in response to a change in posture, either the pulse width can be increased or as demonstrated earlier a high frequency train using a shorter pulse width could be used.

The present invention further recognises that cutaneous sensation is suppressed by movement and by sensory input, that the level of suppression is dependent on the intensity of the movement or sensory input, and that movement induced suppression attenuates both flutter and pressure. The reduction in the pressure sensation was 30, 38 and 79% for slow, medium and rapid movement, respectively. In general, sensory input displays a masking phenomenon where the presence of a large stimulus can mask the perception of a smaller stimulus. This can even happen when the smaller stimulus is presented before the larger stimulus (forward masking). This phenomenon occurs during cutaneous input.

A first embodiment of the invention therefore provides a spinal cord stimulation system which has the ability to detect movement, and to apply or increase electrical stimulation only during the periods where movement is sufficiently strong so as to mask the sensation produced by electrical stimulation. Such a system achieves relief from pain for the individuals implanted but without generation of sensation due to the fact that the sensation which would be perceived by the subject when they are stationary is below threshold for perception during movement.

There are a number of ways in which the movement of the individual might be detected. One method is to use an accelerometer, which senses movement of the stimulator, another is to use the impedance of the electrode array which changes as a result of the motion in the epidural space of the spinal cord. A third method for detecting movement is to use the modulation of the evoked compound action potential. Closed loop neuromodulation systems have been developed which employ recordings of the compound action potential to achieve a constant recruitment, for example as described in International Patent publications WO2012155183 and WO2012155188, the contents of which are incorporated by reference in their entirety. The amplitude of the ECAP has been shown to sensitively vary with the changes in posture. The amplitude can thus be used to detect movements and time the delivery of bursts of stimuli to coincide with those movements. Measurement of the ECAP provides a method of directly assessing the level of recruitment in the dorsal columns of the spinal cord depending on posture. A further method for detecting movement, which is also suitable for detecting sensory input, is to monitor neural activity on the nerve which has not been evoked by the neurostimulator, for example in the manner described in the present applicant's Australian provisional patent application no. 2014904595, the content of which is incorporated herein by reference. Such non-evoked neural activity can result from efferent motor signals or afferent sensory or proprioceptive signals, which present opportunities at which masking can occur and thus define times at which delivery of an increased stimulus dosage may be appropriate.

Figure 8:
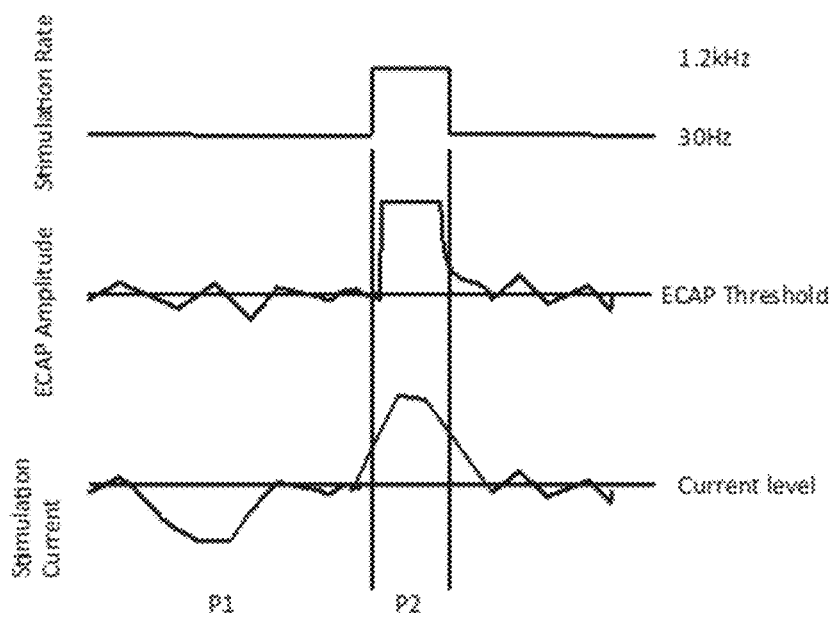
FIG. 8 illustrates monitoring of a stimulation current required to maintain a constant ECAP response.

The algorithm in this embodiment works as follows. Feedback control of a sub paraesthesia amplitude of ECAP is established with the patient stationary. Movement is detected by monitoring the stimulation current, which is constantly adjusted to maintain a constant ECAP response. A set point is established for the amplitude of the change over time which when reached indicates a sufficiently rapid movement to change stimulation parameters. A change in the current may be insufficient to meet the criteria for detecting a sufficiently large movement (as occurs in time period P1 in FIG. 8) or it may meet or exceed the criteria (as occurs in time period P2 in FIG. 8).

On detection of this change a new stimulation condition is set, by adjusting stimulation parameters. The stimulation parameters may be any of those which effect the recruitment of dorsal column fibres such as the amplitude, pulse width, stimulation frequency or combination thereof. The stimulator outputs a stimulus train at the new settings for a period of time. The output can be controlled in a feedback loop as well so that a constant level of recruitment is achieved. The timing for the increased period of stimulation is adjusted so that it ceases in a short period coincident with the movement detected, and terminates before the motion ceases, such that it is not perceived by the individual.

The timing and amplitude can be set by a number of means, such as a fixed amplitude applied for a fixed time, an amplitude which is adjusted proportionally to the amplitude of the measured ECAP or movement and terminated after a fixed interval, or a fixed amplitude of stimulation and termination after the variation, being the first derivative over time of the ECAP amplitude, drops. Recall that the stimulation parameters are adjusted on reaching a set level of variation. Thus, a fixed ECAP amplitude can be adjusted via feedback which is terminated when the 1st derivative over time of the applied current drops below a set level.

After the stimuli train is delivered the system reverts to a stimulation mode that is below perception threshold to monitor for further changes in postures, and the sequence is repeated. The adjustment of the stimulation parameters can be controlled over time (ramp up and ramp down) or other time varying function.

Without intending to be limited by theory, current postulated mechanisms of action of SCS are based on the Aβ fibre activity in the dorsal column resulting, via synaptic transmission, in the release of GABA, an inhibitory neurotransmitter, in the dorsal horn. GABA then reduces spontaneous activity in wide dynamic range neurons and hence produces pain relief. The kinetics of GABA mediated inhibition are unknown, however there is a post switch off effect from SCS which can be quite prolonged in some patients. This suggests that build-up of GABA may be possible over short periods, which would lead to longer term pain inhibition. If the quanta for GABA release is proportional to the stimuli then it is instructive to compare tonic continuous stimulation to bursts of higher frequency stimulation. Continuous tonic stimulation provides 216 000 stimuli over a one hour period at a stimulation frequency of 60 Hz, whereas at 1.2 kHz delivery of the same number of stimuli is achieved in three minutes. Given control over stimulus delivery as described above then 3 minutes of activity in an hour would result in the same number of supra-threshold stimuli delivered with tonic stimulation. Hence a higher frequency stimulus burst may be as efficacious as tonic stimulation but with a much shorter elapsed duration of stimuli.

The use of ECAPS allows the dosage of stimuli applied to the recipient during the day to be carefully controlled and additional stimuli could be applied if the number of stimuli falls below a target level which is required to achieve optimal therapy. This may occur because an individual is not active enough, or because the system set points are not optimally adjusted. Given such conditions the system can alert the user or the clinician or even revert to periods of tonic continuous super threshold stimulation.

In some embodiments the applied therapeutic stimuli may be supra threshold stimuli for neural activation, however in other embodiments sub threshold stimuli may be applied for psychophysical perception in other therapeutic areas.

Figure 9:
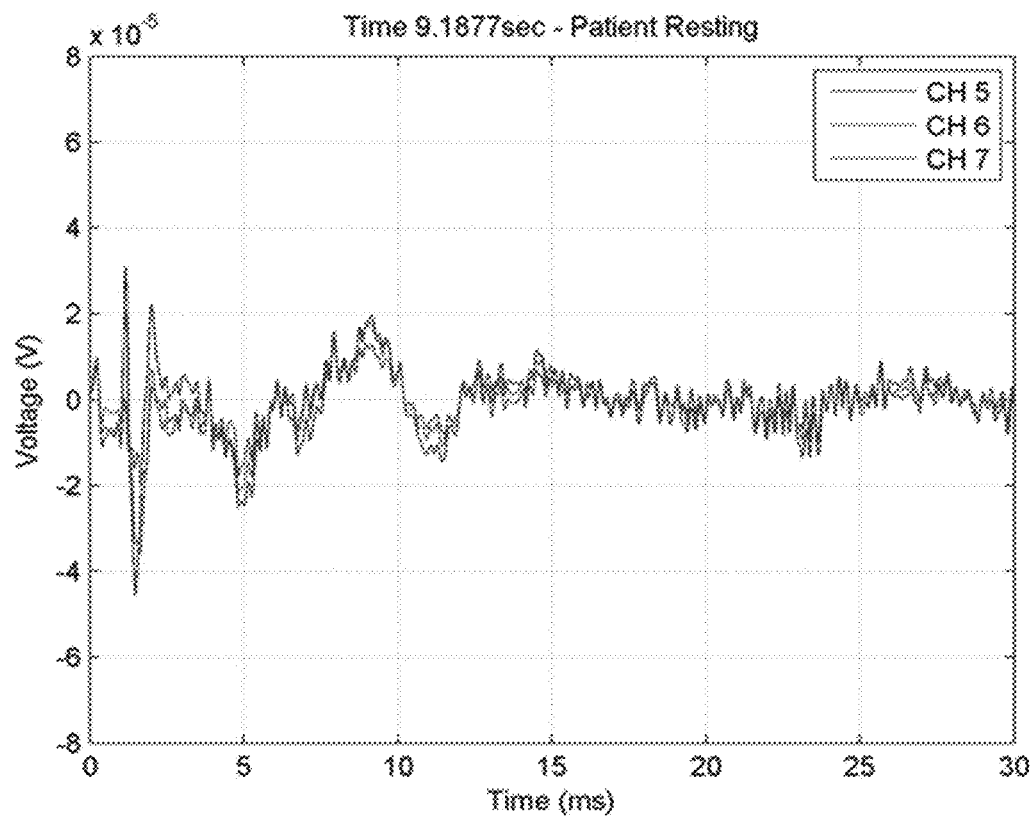
FIG. 9 show examples of ECAP recordings with a patient at rest.

ECAP measurements as described above may be used as a method to time the application of pain relieving stimuli to coincide with detected movement. A number of other methods may also be used including a measure of the patient's own non-evoked neural activity. FIG. 9 show examples of ECAP recordings with a patient at rest and FIG. 10 shows ECAP recordings with the patient walking on the spot.

Figure 10:
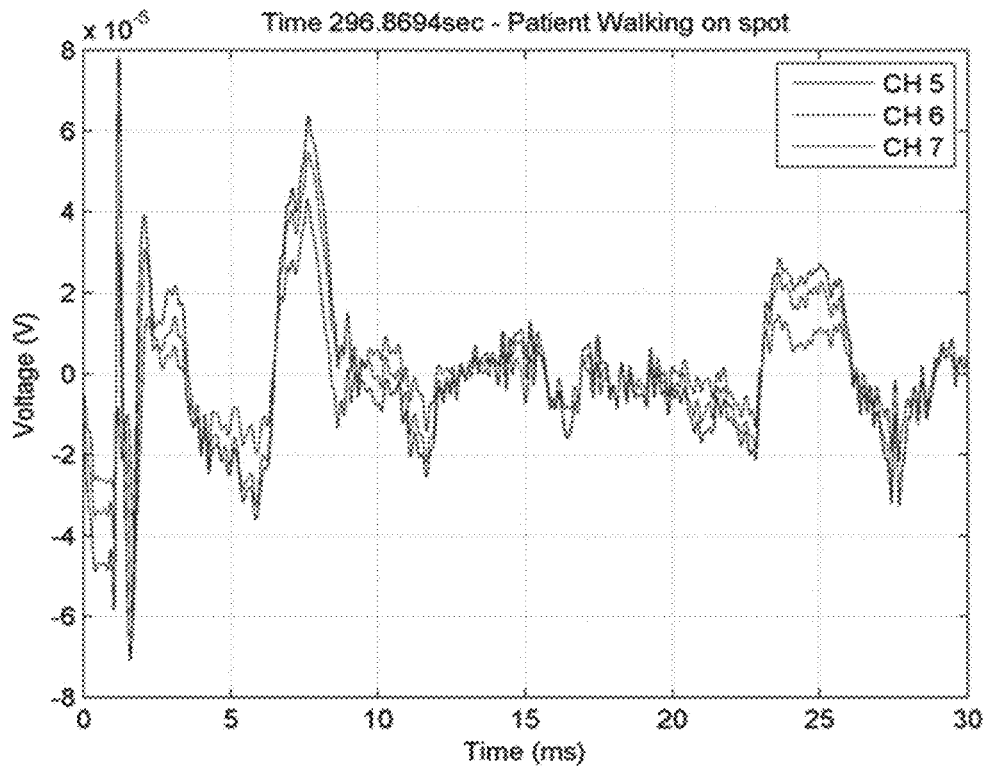
FIG. 10 shows ECAP recordings with the patient walking on the spot.

In FIGS. 9 and 10 there is a significant difference in the amplitude of the noise due to non-evoked activity immediately post the stimulus with the patient walking on the spot. Simple visual inspection shows that in FIG. 9 during the time period 15-20 s the neural activity amplitude is generally less than 5 microvolts, whereas during the same period in FIG. 10 the neural activity amplitude often exceeds 10 microvolts. A number of automated techniques may be used to determine the amplitude of the non-evoked neural activity. The amplitude can be directly measured by determining the maximum and minimum values of the response or alternatively the RMS (root mean square) can be determined over a window.

The non-evoked activity can be measured on a continuous basis without outputting stimuli. In this manner the extent of activity or movement of the individual can be assessed on a continuous basis, so that sufficiently swift movements can be detected and used as triggers for increased stimulus dosing.

Figure 11A:
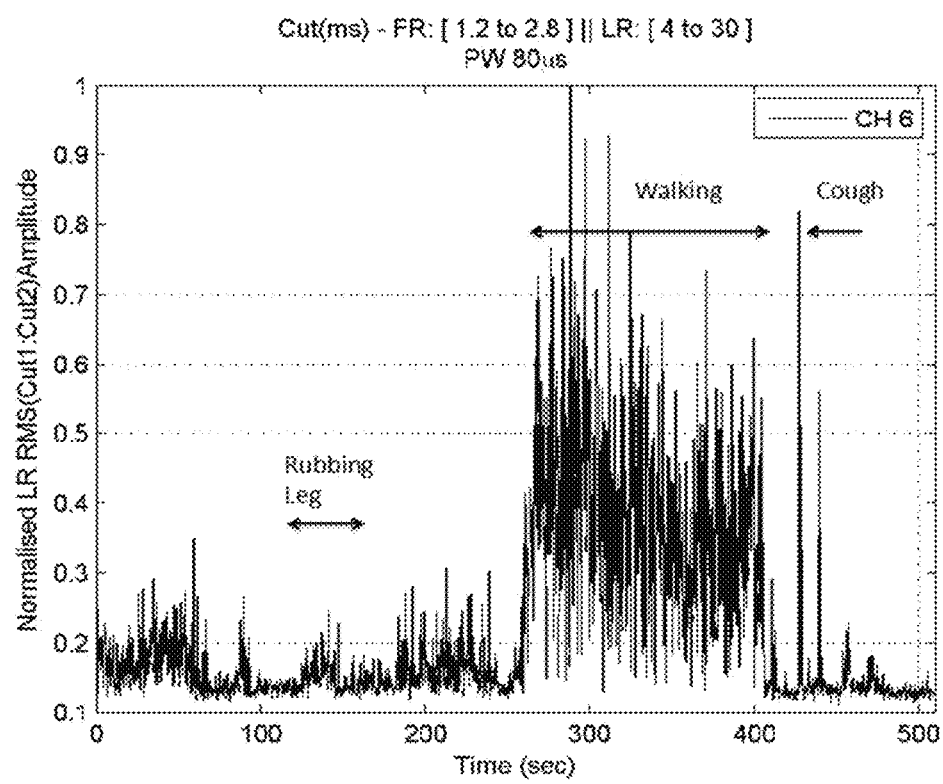
FIGS. 11a and 11b show non evoked activity measured from a patient.
Figure 11B:
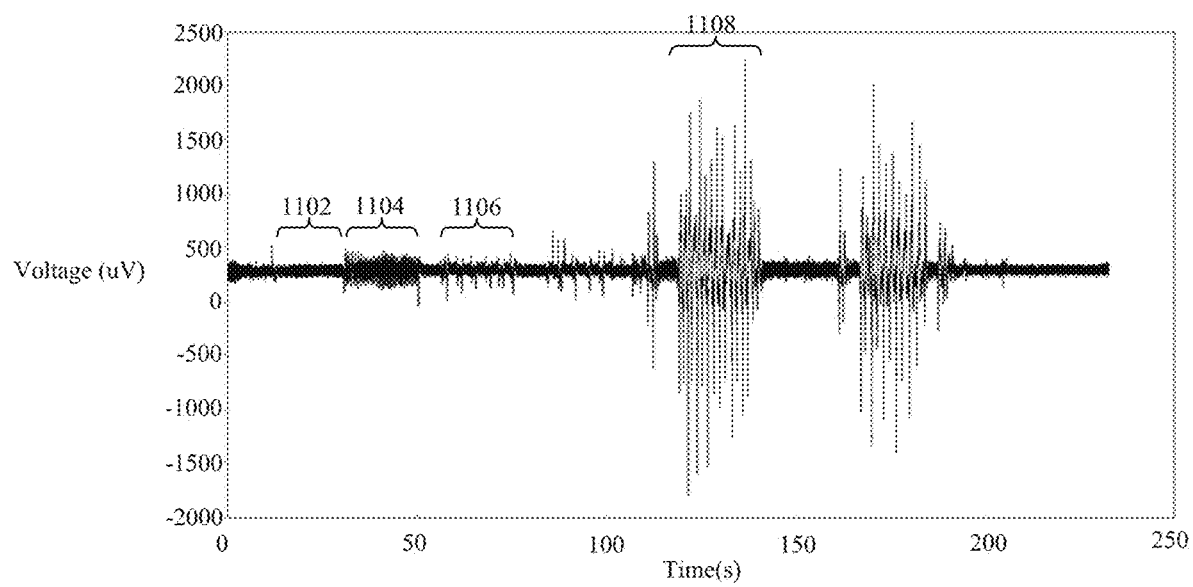

FIG. 11a shows non evoked activity measured from a patient, and shows the RMS non-evoked activity for an individual undergoing a range of movement activities from rubbing the leg to walking on the spot and coughing. As is evident in the figure the RMS signal is much larger when the patient is active and walking on the spot. FIG. 11b is another illustration of non-evoked neural activity measured from a patient, and shows the RMS non-evoked activity for an individual whom at 1102 is not moving, at 1104 is rubbing their leg, at 1106 is lifting one leg while seated and at 1108 is walking. In particular FIG. 11b shows that sensory input of rubbing the leg at 1104, and motor and/or proprioceptive input of lifting the leg at 1106, are each only subtly different from times of no movement as shown at 1102, and some embodiments of the present invention are specifically configured to address this problem.

In one embodiment, an algorithm which exploits the non-evoked activity operates as follows:
 i. The implant system monitors the non-evoked activity (N) until a threshold measure of activity is reached ($T_{nn}$).
 ii. On reaching the threshold, stimuli are generated and, after any evoked response has concluded, the magnitude of the post-stimulus non-evoked activity is re-measured ($N_s$).
 iii. Stimuli are generated at a rate ($R_s$) until the non-evoked activity ($N_s$) falls below a second threshold measure of activity ($T_{ns}$) at which point stimulation ceases. $T_{ns}$ typically takes a smaller value than $T_{nn}$, selected to provide a suitable degree of hysteresis.
 iv. The implant system then continues to monitor the non-evoked activity and returns to step (i).

The stimulus rate ($R_s$) may be a fixed rate or it may also be set to vary with the magnitude of the non-evoked activity The amplitude of the evoked activity can be used to control the amplitude of the stimulus generated with each successive stimuli in a feedback loop as has been described in International Patent Publication No. WO2012155188, for example. The advantage of employing a feedback loop in such a manner is to keep the ECAP amplitude constant during a period of active movement during which it is known to vary considerably.

The parameters for this algorithm can be determined in the following manner
 i. The patient is programmed with a traditional method with continuous stimulation with patient at rest. The stimulus location and amplitude is adjusted in order to obtain paraesthesia coverage of the pain full area. The amplitude of the ECAP ($E_a$) for obtaining pain relief is noted.
 ii. The stimulation is turned off and the range of non-evoked activity is measured. The threshold $T_{nn}$ is set such that it is above the base line of non-evoked activity with the patient at rest.

The presence of the non-evoked activity is the result of movement of and/or sensory input to the individual. Movement also affects the amplitude of the evoked activity, so that if the evoked activity is controlled with a feedback loop, then a change in the current or other stimulus parameter which is set to maintain a constant amplitude can be used to monitor for a change in movement and set the point for cessation of the stimuli.

By delivering increased stimuli only at times at which movement and/or sensory input is detected, the present invention provides for a considerably reduced power budget. For example if movement is detected every 15 seconds, and the delivered stimulus comprises 5 stimuli, the system will deliver 20 stimuli per minute as compared to 1200 stimuli per minute for a continuous 20 Hz stimulus regime, i.e. 98.3% fewer stimuli.

FIG. 12a illustrates the threshold 1210 of dorsal column activation, which varies over time for example with postural changes. At times 1222, 1224 this threshold 1210 drops below the stimulus level 1230. The present invention may initiate or increase the stimulus regime during these periods 1222, 1224, either throughout the entire period as shown in FIG. 12b or for example at the start and/or finish of the period as shown in FIG. 12c. It is to be noted that each affected fibre will also respond in a corresponding manner albeit at slightly different times depending on the distance of the electrode from that fibre and the time at which the user movement causes the fibre to come within the effective stimulus range of the electrode. The delivered stimuli 1240, 1242 delivered in FIG. 12b comprise a burst of high frequency stimuli at 10 kHz, 40 µs pulse width and 2 mA amplitude. Such stimuli are configured to effect a blockade during respective time periods 1222 and 1224, so that in FIG. 12b only a single action potential 1250, 1252 is produced in each time period 1222, 1224 and the fibre is then blockaded for the remainder of the respective time period.

In FIG. 12c an alternative stimulus regime is applied, with stimuli being applied only at threshold crossings, these being the moments at which the user is actually moving from one posture to the next. In accordance with the first aspect of the invention, the sequences of stimuli 1260, 1262, 1264, 1266 deliver an increased stimulus dosage during times of movement, so that an increased number of action potentials 1270 are evoked at such times. This embodiment recognises that, during movement, the psychophysics of perception can result in the individual perceiving a reduced sensation from a given stimulus as compared to when the same stimulus is applied while the individual is not moving. However, the benefits of delivering a large dosage of stimuli remain for a period of time after conclusion of the stimuli.

Figure 13:
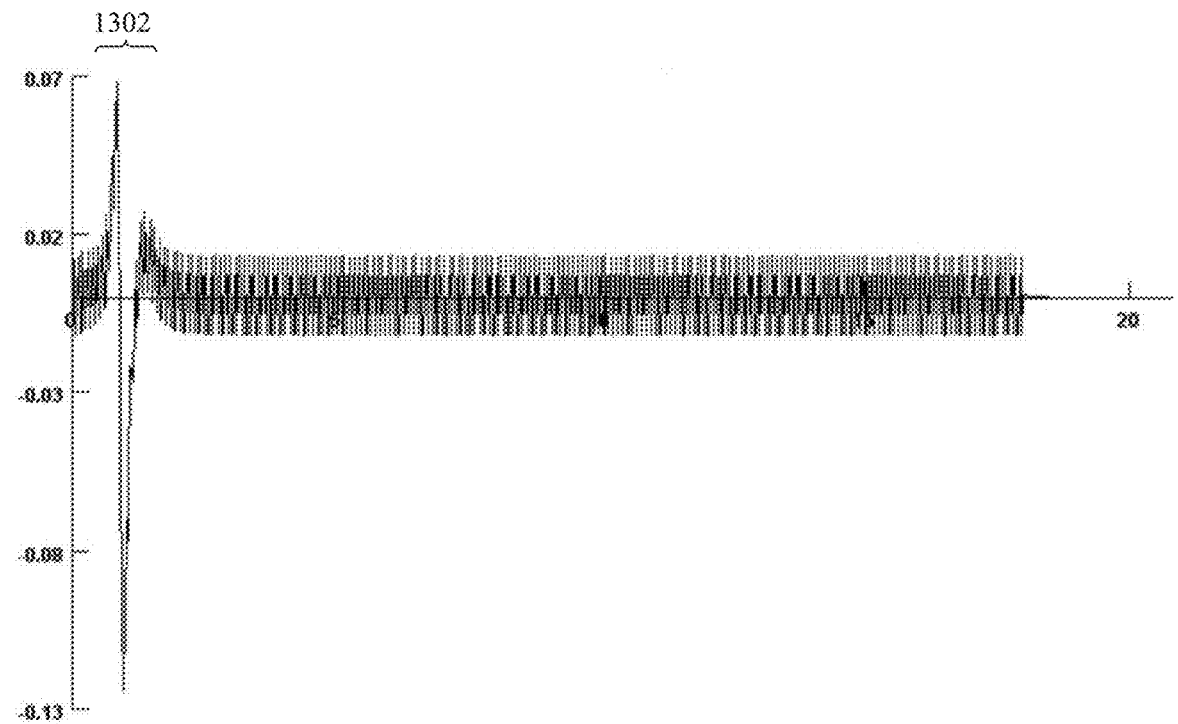
FIG. 13 illustrates the neural voltage recorded during a blockade.
Figure 14:
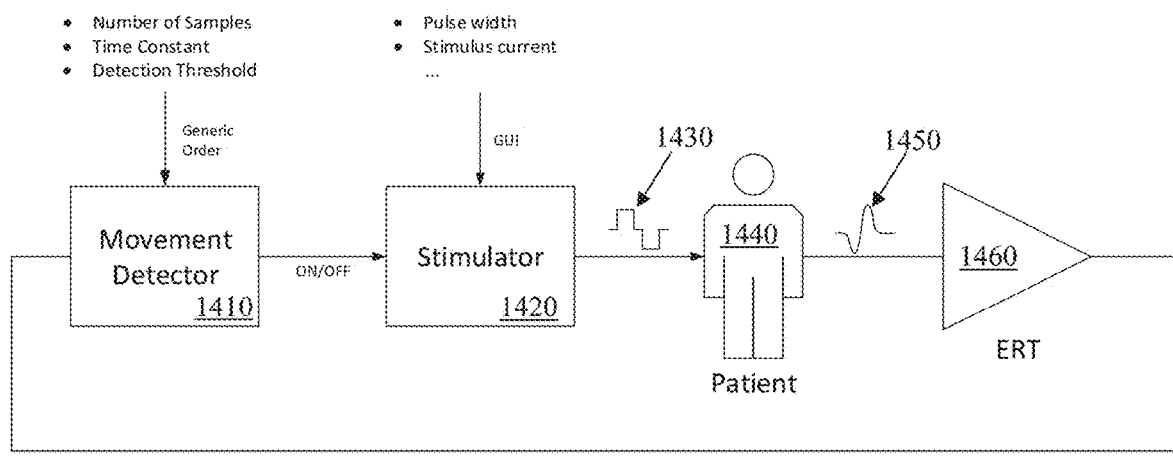
FIG. 14 illustrates operation of a motion activity detector.

FIG. 13 illustrates the neural voltage recorded during a blockade as may be produced by stimuli 1240, 1242. As can be seen the period of the high frequency sequence of stimuli is less than the period of the action potential 1302. Thus, while a first stimulus of the sequence generates action potential 1302, each subsequent stimulus alters a membrane potential of the neural tissue without causing depolarisation of the neural tissue and without evoking an action potential, each subsequent stimulus being delivered prior to recovery of the membrane potential of the neural tissue from a preceding stimulus.

FIGS. 14-17 illustrate operation of a motion activity detector 1410 which detects movement of a patient 1440 by analysis of observed neural responses 1450 evoked by applied stimuli 1430. The algorithm performed by detector 1410 enables stimulation to be delivered only when movement-related slow spinal cord potentials are recorded, and otherwise disables stimulation. Movement-related spinal cord potentials are defined in this embodiment as signals greater than 200 $\mu V_{p-p}$, normalised for lead position, with a band width between 1 and 30 Hz.

One goal of the detector 1410 is to accurately detect movement of the particular limb or part of the body associated with the area that pain occurs, e.g. for leg pain the detector 1410 seeks to detect walking, lifting the leg, and the like. The detector 1410 is also configured to detect movement quickly enough to be able to commence stimulation while the movement is still occurring. The detector 1410 is also parameterised, so that the algorithm can be made to work for patients with varying stimulation parameters.

The detector 1410 operates by applying a sequence of stimuli over time and obtaining a neural response amplitude measurement after each stimuli. The sequence of neural response amplitudes obtained in this manner over the course of 30 seconds is plotted at 1502 in FIG. 15. During this period the patient was walking on the spot. The neural response signal 1502 is low pass filtered, differentiated, and rectified, to produce rectified differentiated neural response signal 1504. The differentiator allows movements to be detected early, and the rectifier ensures that both negative and positive-going signals are captured. The gradient value m[n], i.e. signal 1504, is then fed to an envelope detector with the following equation:

$$l[n] = \begin{cases} m[n], & m[n] > l[n-1] \\ \alpha l[n-1] + (1-\alpha)m[n-1], & m[n] \le l[n-1] \end{cases}$$

Figure 15:
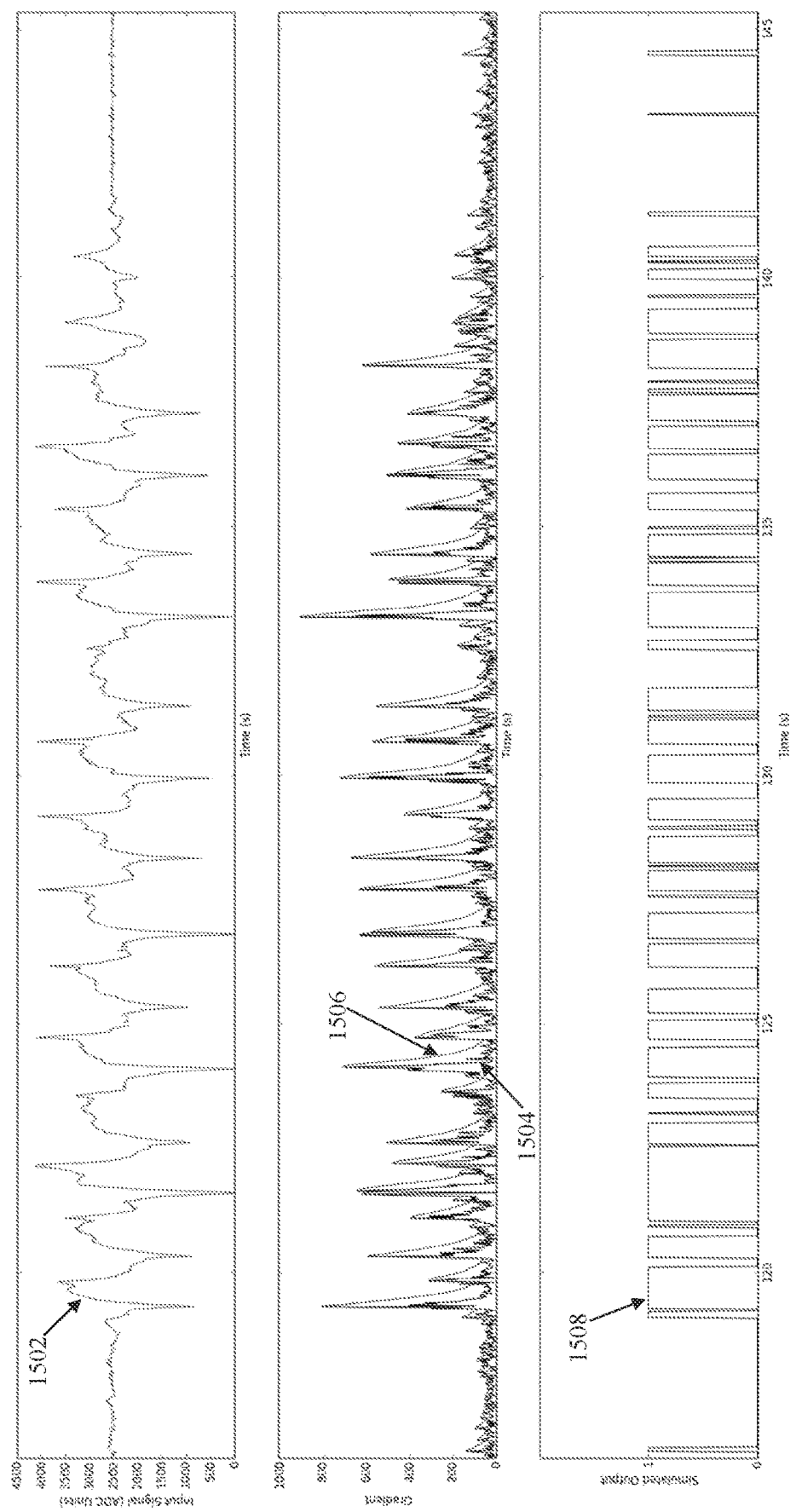
FIGS. 15-17 illustrate neural response signals observed during patient movement, and the resulting stimuli regimes delivered by the detector of FIG. 14.

The parameter $\alpha$ is a value between 0 and 1. Values closer to one will cause a slower envelope delay and thus cause the stimulus to be applied for a longer period after each detection. The envelope 1506 produced in the above manner from the differentiated signal 1504 is shown in FIG. 15. The detector output 1508 is thresholded from envelope 1506, where a detector output value of 1 causes stimuli to be applied, and an output of zero disables stimuli delivery. As can be seen in this embodiment, the detector output 1508 thus causes stimuli to be selectively delivered only at times when movement is detected.

Figure 16:
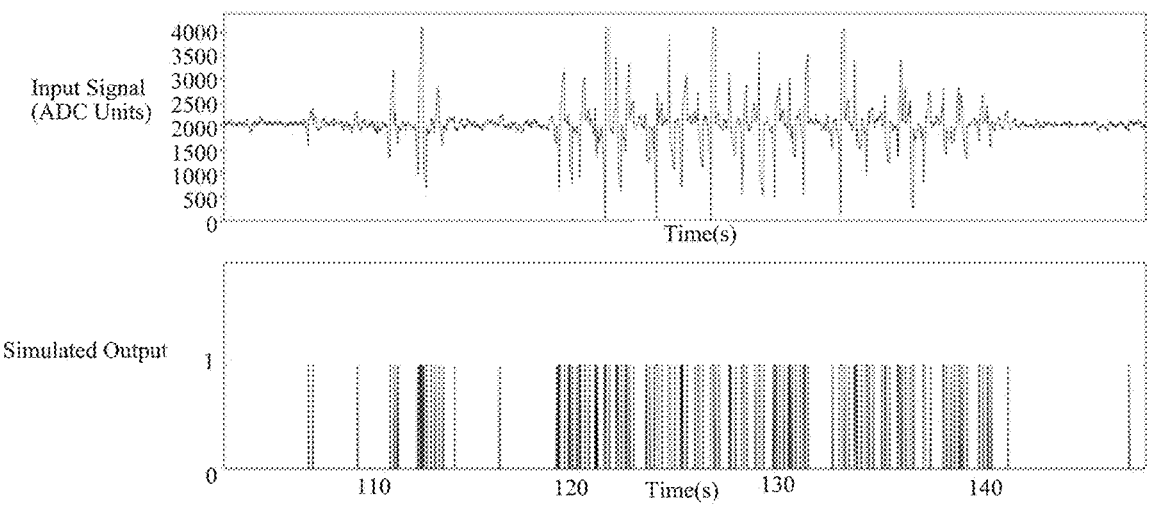
Figure 17:
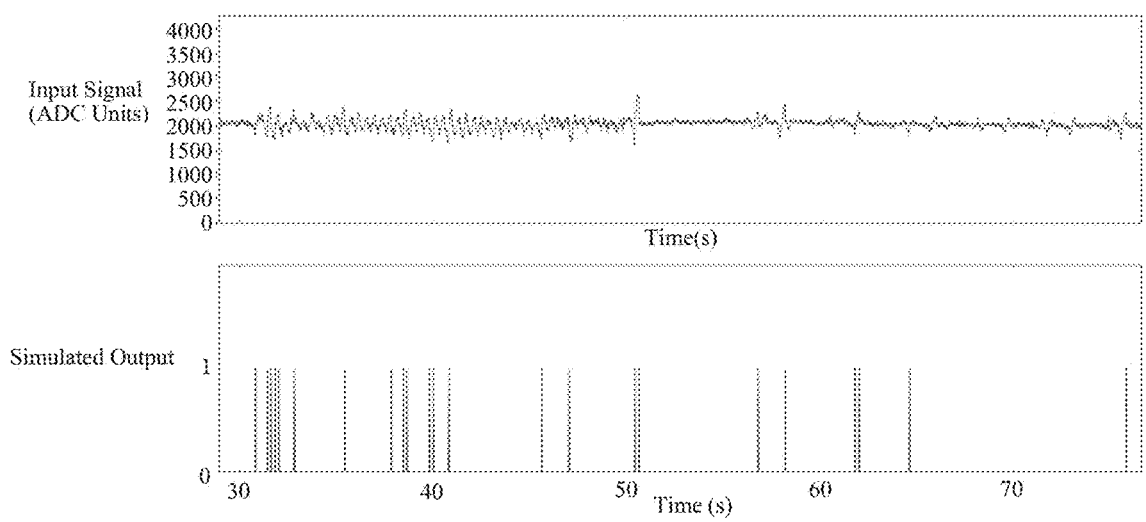

Tuning of the threshold and the parameter $\alpha$ allows the stimulus dosing to be adjusted. For example FIGS. 16 and 17 show the algorithm output during various patient movements with parameters which give rise to smaller or more sparse periods of stimulation than seen in 1508 in FIG. 15.

Other embodiments of the activity detector may also provide a movement magnitude output, indicating the magnitude of the movement, which may be used to modulate the magnitude or duration of the stimulation, or other stimulation parameters.

Figure 18:
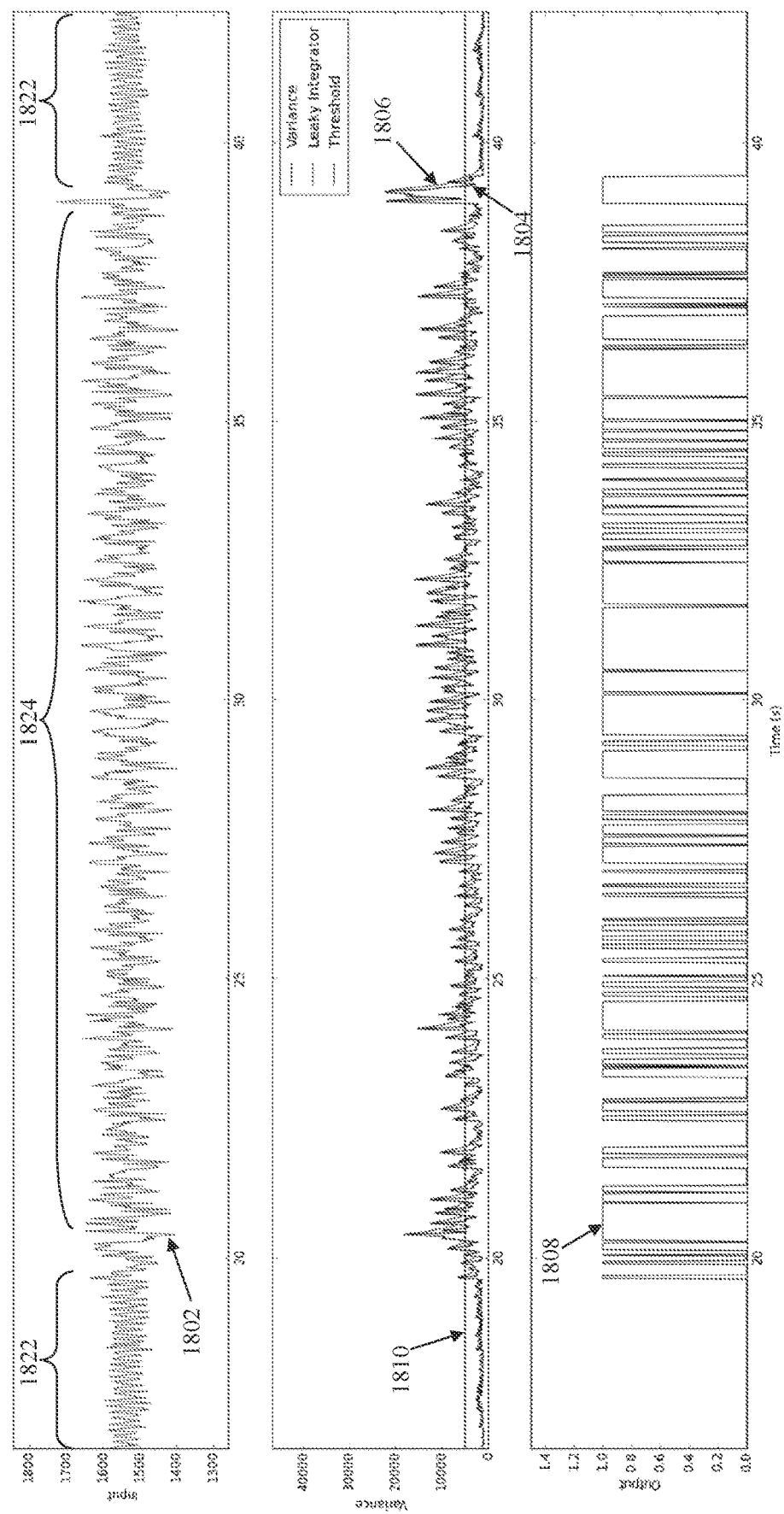
FIG. 18 illustrates operation of a neural activity detector in accordance with another embodiment of the present invention.

As can be seen the embodiment of FIGS. 14-17 is effective for periods when the patient is walking. FIG. 18 illustrates another embodiment which is further operable to appropriately detect sensory input such as rubbing the leg. In this embodiment, the detector operates by applying a sequence of stimuli over time and obtaining a neural response amplitude measurement after each stimuli. The sequence of neural response amplitudes obtained in this manner over the course of about 30 seconds is plotted at 1802 in FIG. 18. Prior to about 19 seconds into the measurements, and after about 39 seconds of measurements 1802, the patient was inactive as indicated by 1822. During period 1824 the patients rubbed their leg. The difference in signal 1802 between period 1822 and 1824 is fairly subtle, however the sensory input of leg rubbing presents an opportunity to deliver stimuli during period 1824 in order to take advantage of masking. Therefore the present embodiment is configured to analyse the measurements signal 1802 and to differentiate a period of sensory input 1824 from periods 1822 of inactivity.

To achieve this goal, the embodiment of FIG. 18 obtains the neural measurements 1802 at 60 Hz. Each measurement, or sample x[n], is saved to a circular buffer of a length defined by a Detection Window Length parameter, N. Each new sample is used to update a moving average using the formula:

$$avg[n] = \frac{1}{2}avg[n-1] + \frac{1}{2}x[n]$$

The two-sample moving average is beneficial in minimising processing time. Next, the variance 1804 of the signal 1802 is calculated from all the samples in the circular buffer, and using the above-noted moving average:

$$\mathrm{var}[n] = \frac{1}{N}\sum_{i=0}^{N-1}(x[n-i]-avg[n])^2$$

The variance 1804, var[n], is then fed to an envelope detector with the following equation:

$$l[n] = \begin{cases} \mathrm{var}[n], & m[n] > l[n-1] \\ (1-\alpha)l[n-1] + \alpha\,\mathrm{var}[n], & m[n] \le l[n-1] \end{cases}$$

The parameter $\alpha$ is a value between 0 and 1, and can be adjusted whereby smaller values will cause the stimulus to be applied for a longer period after an initial detection. The output of the envelope detector is shown at 1806 in FIG. 18.

The detector output 1808 is produced by being thresholded from envelope 1806 by comparison to threshold 1810, where a detector output value of 1 causes stimuli to be applied, and an output of zero disables stimuli delivery. The threshold can be adjusted to suit given hardware and/or a given patient. As can be seen in this embodiment, the detector output 1808 thus causes stimuli to be selectively delivered only at times when sensory input is occurring. In particular, in this embodiment the detector output 1808 appropriately disables stimuli during period 1822, while taking good advantage of the masking opportunity afforded by leg rubbing during period 1824 to deliver an increased dosage of stimulation, despite the somewhat subtle differences in signal 1802 between the periods of inactivity 1822 and the period of leg rubbing 1824.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method of applying therapeutic neural stimuli, the method comprising:
   monitoring, by a control unit, for at least one of sensory input and movement of a user by measuring neural activity upon a neural pathway of the user with at least one electrode positioned alongside the neural pathway; and
   applying, by the control unit, therapeutic neural stimuli to the neural pathway with the at least one electrode based on the at least one of sensory input and movement of the user,
   wherein the measured neural activity comprises non-evoked neural activity.

2. The method of claim 1, wherein the monitoring comprises directly measuring an amplitude of the non-evoked neural activity by determining the maximum and minimum values of the non-evoked neural activity over a window.

3. The method of claim 1, wherein the monitoring comprises directly measuring an amplitude of the non-evoked neural activity by determining a root mean square of the non-evoked neural activity over a window.

4. The method of claim 1, wherein the monitoring comprises directly measuring an amplitude of the non-evoked neural activity until a threshold measure of activity is reached.

5. The method of claim 4, wherein the threshold measure of activity is set such that it is above a base line of non-evoked activity with the user at rest.

6. The method of claim 1, wherein the applying comprises, in response to detection of at least one of sensory input and a user movement, delivering an increased stimulus dosage within a period of time corresponding to a duration of time for which the detected sensory input or user movement gives rise to masking, the increased stimulus dosage being configured to give rise to increased neural recruitment.

7. The method of claim 6, wherein the increased stimulus dosage is effected by increasing one or more of an amplitude of the neural stimuli, a pulse width of the neural stimuli, and a frequency of the neural stimuli.

8. The method of claim 7, wherein the increased stimulus dosage comprises a burst of high frequency stimuli.

9. The method of claim 7, wherein at times when neither sensory input nor movement is detected, stimuli are delivered at a reduced dosage.

10. The method of claim 6, wherein at times when neither sensory input nor movement is detected, no stimuli are delivered.

11. The method of claim 6, further comprising:
    monitoring a cumulative stimulus dosage delivered to the user, and
    using the cumulative stimulus dosage as a basis to define a required stimulus regime either during or between movements in order to deliver a desired total stimulus dosage.

12. The method of claim 6, wherein the period of time within which the increased stimulus dosage is delivered is a predefined approximation of the duration of a typical human movement.

13. The method of claim 6, wherein the period of time for which the increased stimulus dosage is delivered is adaptively determined by performing the further step of detecting a cessation of sensory input or movement by the user, and in turn ceasing the delivery of the increased stimulus dosage.

14. The method of claim 6, wherein the increased stimulus dosage is delivered at select moments within the period of time.

15. A device for applying therapeutic neural stimuli, the device comprising:
    at least one electrode configured to be positioned alongside a neural pathway of a user; and
    a control unit configured to:
        monitor for at least one of sensory input and movement of the user by measuring neural activity upon a neural pathway of the user, and
        apply therapeutic neural stimuli to the neural pathway based on the at least one of sensory input and movement of the user,
    wherein the measured neural activity comprises non-evoked neural activity.

16. The device of claim 15, wherein the control unit is configured to monitor by directly measuring an amplitude of the non-evoked neural activity by determining the maximum and minimum values of the non-evoked neural activity over a window.

17. The device of claim 15, wherein the control unit is configured to monitor by directly measuring an amplitude of the non-evoked neural activity by determining a root mean square of the non-evoked neural activity over a window.

18. The device of claim 15, wherein the control unit is configured to monitor by directly measuring an amplitude of the non-evoked neural activity until a threshold measure of activity is reached.

19. The device of claim 15, wherein the control unit is configured to apply the therapeutic stimuli by, in response to detection of at least one of sensory input and a user movement, delivering an increased stimulus dosage via the at least one electrode within a period of time corresponding to a duration of time for which the detected sensory input or user movement gives rise to masking, the increased stimulus dosage being configured to give rise to increased neural recruitment.

20. The device of claim 19, wherein the control unit is configured to effect the increased stimulus dosage by increasing one or more of an amplitude of the neural stimuli, a pulse width of the neural stimuli, and a frequency of the neural stimuli.

* * * * *